(12) United States Patent
Schmidt

(10) Patent No.: US 9,232,920 B2
(45) Date of Patent: Jan. 12, 2016

(54) SELF-EXPANDING MULTI-CHANNEL RF RECEIVER COIL FOR HIGH RESOLUTION INTRA-CARDIAC MRI AND METHOD OF USE

(75) Inventor: Ehud J. Schmidt, Newton, MA (US)

(73) Assignee: General Electric Company, Schenectady, NY (US)

( * ) Notice: Subject to any disclaimer, the term of this patent is extended or adjusted under 35 U.S.C. 154(b) by 3796 days.

(21) Appl. No.: 10/708,723

(22) Filed: Mar. 19, 2004

(65) Prior Publication Data

US 2005/0215886 A1    Sep. 29, 2005

(51) Int. Cl.
| | |
|---|---|
| A61B 5/00 | (2006.01) |
| A61B 5/055 | (2006.01) |
| G01R 33/28 | (2006.01) |
| G01R 33/34 | (2006.01) |

(52) U.S. Cl.
CPC ............. *A61B 5/6858* (2013.01); *A61B 5/055* (2013.01); *G01R 33/287* (2013.01); *A61B 5/7285* (2013.01); *G01R 33/34084* (2013.01)

(58) Field of Classification Search
USPC ......................................... 600/421, 424, 428
See application file for complete search history.

(56) References Cited

U.S. PATENT DOCUMENTS

| | | | |
|---|---|---|---|
| 5,271,400 A | 12/1993 | Dumoulin et al. | |
| 5,307,808 A | 5/1994 | Dumoulin et al. | |
| 5,318,025 A | 6/1994 | Dumoulin et al. | |
| 5,353,795 A | 10/1994 | Souza et al. | |
| 6,292,683 B1* | 9/2001 | Gupta et al. | 600/410 |
| 6,516,210 B1* | 2/2003 | Foxall | 600/410 |
| 6,516,213 B1* | 2/2003 | Nevo | 600/424 |
| 6,628,980 B2* | 9/2003 | Atalar et al. | 600/423 |
| 2003/0120146 A1* | 6/2003 | Dumoulin | 600/410 |
| 2004/0046557 A1* | 3/2004 | Karmarkar et al. | 324/322 |

FOREIGN PATENT DOCUMENTS

| | | |
|---|---|---|
| JP | 1994261900 A | 9/1994 |
| JP | 08-076994 | 3/1996 |
| JP | 10149283 | 6/1998 |
| JP | 11306000 | 11/1999 |
| WO | WO0173461 A2 | 10/2001 |

OTHER PUBLICATIONS

Martin, A. et al., "An Expandable Intravenous RF Coil for Arterial Wall Imaging", Journal of Magnetic Resonance Imaging, 1998, vol. 8, pp. 226-234.

Quick, H. et al., "Autoperfused Balloon Catheter for Intravascular MR Imaging", Journal of Magnetic Resonance Imaging, 1999, vol. 9, pp. 428-434.

"ZeroTip™ Nitinol Stone Retrieval Basket", Boston Scientific, http://www.bostonscientific.com.

Quick, H. et al., "Endourethral MRI", Magnetic Resonance in Medicine, 2001, vol. 45, pp. 138-146.

(Continued)

*Primary Examiner* — Long V Le
*Assistant Examiner* — Ellsworth Weatherby
(74) *Attorney, Agent, or Firm* — Ziolkowski Patent Solutions Group, SC

(57) ABSTRACT

A system and method of use for a probe is disclosed that includes a self-expanding housing constructed to permit fluid flow therethrough and constructed for insertion into a subject to be imaged. A plurality of RF coils is attached to the housing to acquire MR data.

12 Claims, 3 Drawing Sheets

(56) References Cited

OTHER PUBLICATIONS

Quick, H. et al., "Vascular Stents as RF Antennas for Intravascular MR Guidance and Imaging", Magnetic Resonance in Medicine, 1999, vol. 42, pp. 738-745.

Shunk, K. et al., "Transesophageal Magnetic Resonance Imaging", Magnetic Resonance in Medicine, 1999, vol. 41, pp. 722-726.
"An Expandable Intravenous RF Coil for Arterial Wall Imaging", http://www.imaging.robarts.ca/~brutt/Research/arterial.html.

* cited by examiner

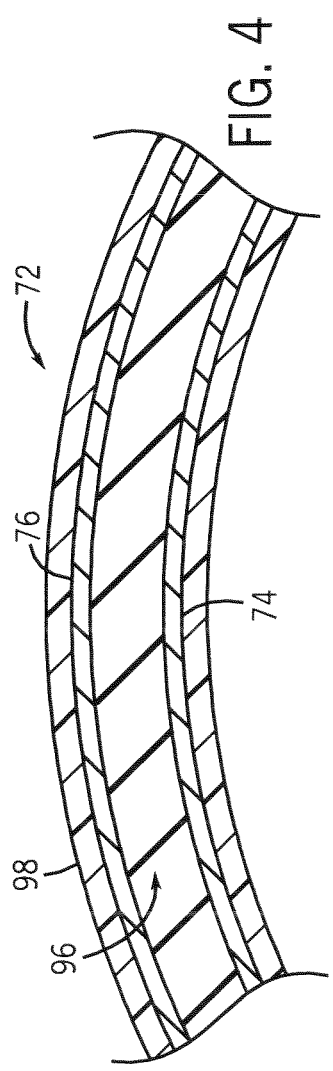
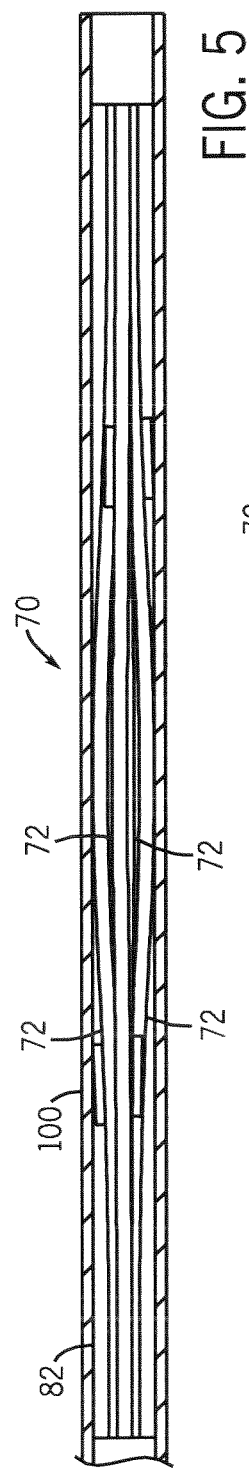
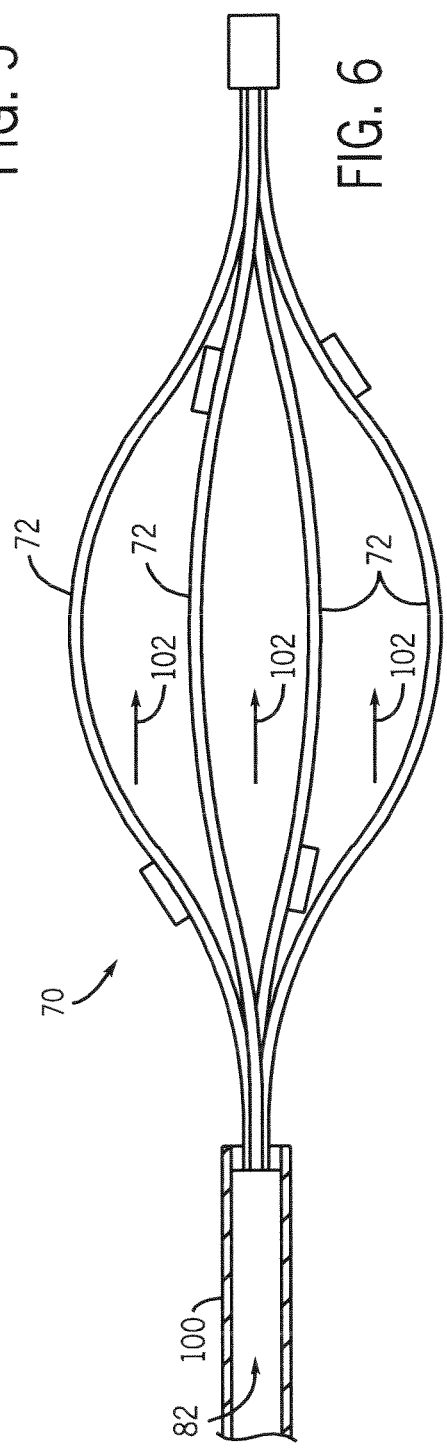

SELF-EXPANDING MULTI-CHANNEL RF RECEIVER COIL FOR HIGH RESOLUTION INTRA-CARDIAC MRI AND METHOD OF USE

BACKGROUND OF INVENTION

The present invention relates generally to MR imaging and, more particularly, to an RF coil assembly capable of self-expansion within a subject to be imaged and capable of minimizing blood flow occlusion by permitting blood flow therethrough.

When a substance such as human tissue is subjected to a uniform magnetic field (polarizing field B0), the individual magnetic moments of the spins in the tissue attempt to align with this polarizing field, but precess about it in random order at their characteristic Larmor frequency. If the substance, or tissue, is subjected to a magnetic field (excitation field B1) which is in the x-y plane and which is near the Larmor frequency, the net aligned moment, or "longitudinal magnetization", MZ, may be rotated, or "tipped", into the x-y plane to produce a net transverse magnetic moment Mt. A signal is emitted by the excited spins after the excitation signal B1 is terminated and this signal may be received by a radio-frequency (RF) coil and processed to form an image.

When utilizing these signals to produce images, magnetic field gradients (Gx, Gy, and Gz) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

High spatial-resolution or high temporal-resolution imaging of heart anatomy and physiology is desired for a variety of purposes. For example, high spatial-resolution imaging may be desired to guide or monitor therapeutic processes in the heart. One major determinant in performing such scans is the intrinsic Signal-to-Noise ratio (SNR) of the RF receiver coil. Current surface mounted RF coils placed on the surface of the torso are limited in SNR due to their physical distance from the heart itself. Also, the use of large coil elements that image more than the heart may negatively affect SNR. As a result, surface coils limit image resolution and may not be desirable for cardiac imaging for use in MR-guided interventional procedures that demand fast, high-resolution imaging.

In an attempt to achieve higher resolution MR images, intra-vascular RF receiver coils have been developed and widely considered preferred for targeted cardiac imaging. Intra-vascular RF coils have been shown to significantly improve SNR by placing the receiving coil in proximity to the target tissue. However, blood flow and associated pulsatility during in-vivo intra-vascular imaging have been obstacles to wide-spread implementation. That is, coil motion and tissue motion caused as a result of blood flow can negatively affect image quality and, thus, the diagnostic and probative value of a resulting image. Further, known intra-vascular RF coils inhibit blood flow when the coil is positioned in the vasculature. As can be appreciated, prolonged blood flow occlusion is undesirable when imaging coronary arteries and within the heart itself.

It would therefore be desirable to have a system and method capable of acquiring MR data using an intra-vascular probe within a moving image target, while minimizing blood flow occlusion within the image target and utilizing known motion of the system to gate image acquisition to reduce image artifacts and blurring.

BRIEF DESCRIPTION OF INVENTION

The present invention provides a system and method of improved MR image acquisition overcoming the aforementioned drawbacks. The invention includes RF coils attached to an expandable housing permitting fluid flow therethrough. The expandable housing is constructed to automatically expand from a compressed position to an expanded position when a sheath is retracted therefrom. A tracking coil is integrated with the system to allow for actively tracking RF coil movement. As a result of tracking RF coil movement, the known motion of the RF coil may be used to gate data acquisition for high-resolution imaging, which is advantageous when the RF coil moves in a beating heart and/or pulsating blood stream. The present invention is particularly useful in conjunction with interventional cardiac therapeutic delivery systems.

Therefore, in accordance with one aspect of the invention, a probe is disclosed that includes a self-expanding housing insertable into a subject to be imaged and constructed to permit fluid flow therethrough. A plurality of RF coils are included that are attached to the housing.

In accordance with another aspect of the invention, an MRI apparatus is disclosed that includes a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images. The RF coil assembly includes a catheter configured for insertion into a blood flow and is constructed to automatically expand to an expanded position from a compressed position. The RF coil assembly also includes a plurality of RF coils connected to the catheter and configured to acquire MR data. Further, the RF coil assembly includes a tracking coil connected to the catheter and configured to indicate RF coil assembly location and movement within an imaging subject.

In accordance with yet another aspect of the invention, a method of using an MR imaging device is disclosed that includes inserting an intra-cardiac MR imaging device into a sheath configured for insertion into an imaging subject to be scanned. The imaging device includes an MR tracking coil and a pair of RF coils attached to an auto-expandable former. The method includes positioning the imaging device within the imaging subject to be scanned and retracting the sheath to allow the former to automatically expand the pair of RF coils to an expanded position. In a further alternate aspect, the MR tracking coil can function, even with the imaging coil folded, and thus provides a vehicle for properly navigating the catheter to the working region of the anatomy.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 4 is an elevational view of FIG. 2 of a bar assembly taken along line 4-4 of FIG. 2.

FIG. 5 is side elevational schematic view of the probe in a compressed position in accordance with the present invention.

FIG. 6 is a side elevational schematic view of the probe in an expanded position in accordance with the present invention.

DETAILED DESCRIPTION

Figure 1:
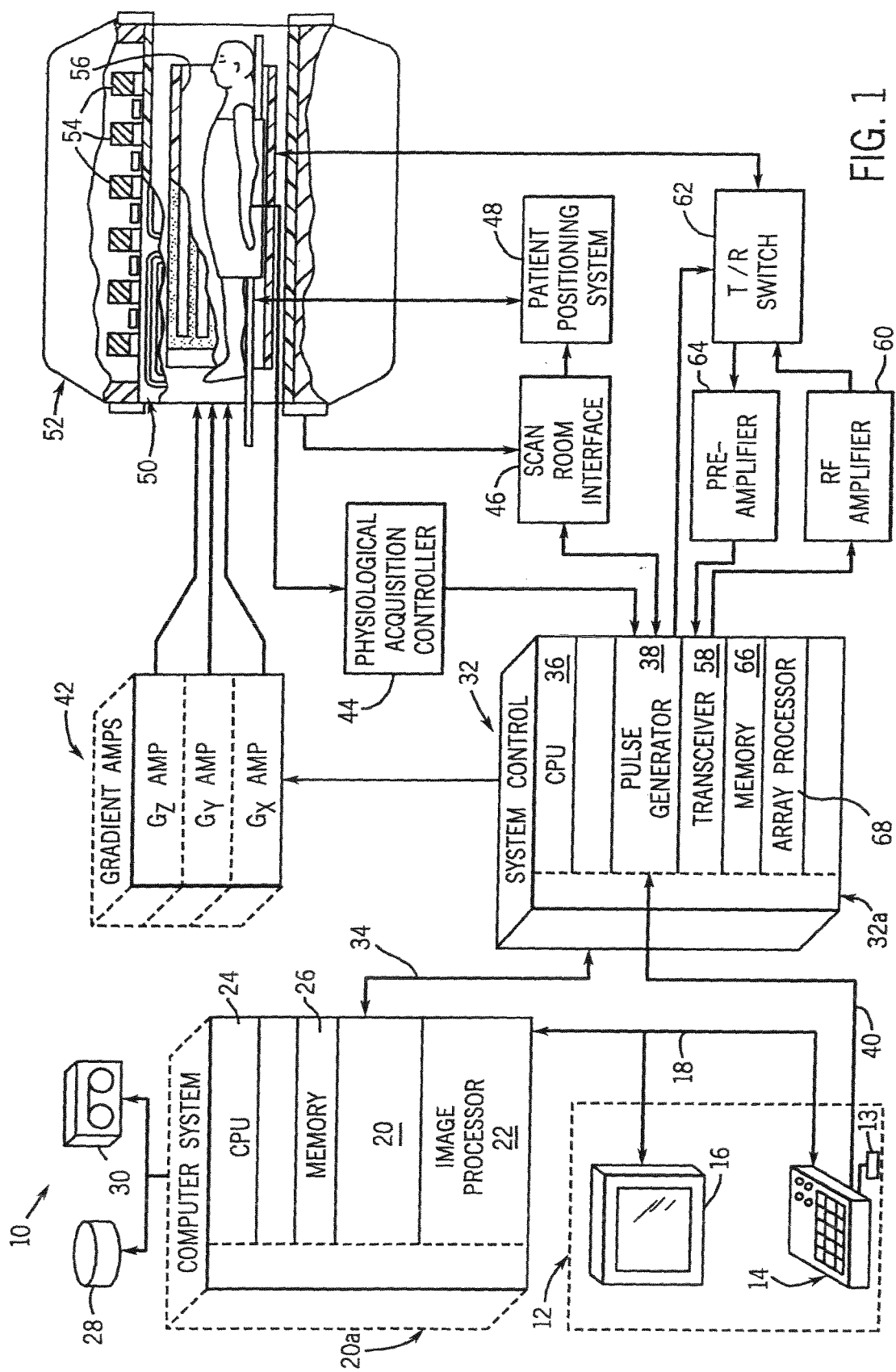
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, an intra-vascular coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rear-ranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

Figure 2:
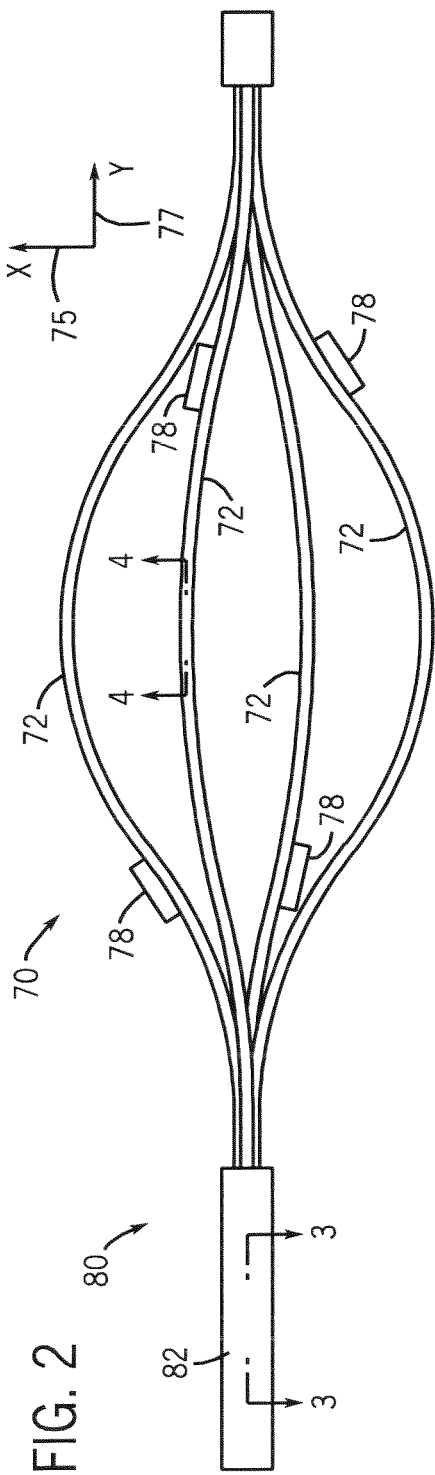
FIG. 2 is an elevational view of an insertable, intra-vascular probe in accordance with the present invention.

Referring to FIG. 2, an insertable, multi-channel intravascular probe 70 in accordance with the present invention and usable with the MRI system 10 of FIG. 1 is shown. The probe 70 includes a plurality of expandable bar assemblies 72. Each bar assembly 72 includes a pair of opposing, expandable bars 74 and an RF coil element 76 attached thereto. The expandable bars 74 are used as an expandable former. In a preferred embodiment, the expandable former has a pair of bar assemblies 72, and the dimensions of the fully expanded former is 2.5 cm. in a minor axis 75 and 6 cm. in a major axis 77. The bar assemblies 72 are constructed so as to reduce a volume occupied thereby to minimize blood flow occlusion when probe 70, as will be described, is in an expanded position within an intra-vascular system, as shown in FIG. 2. The pair of bar assemblies 72 is also constructed to be positioned in non-parallel planes. In a preferred embodiment, the non-parallel planes are orthogonal to each other. MR compatible capacitors 78 are interspersed between sections of the RF coils for RF phase coherency. The probe 70 is attached to a distal end 80 of a catheter 82. Catheter 82 preferably has a 6 Fr., 135 cm. shaft. Catheter 80 eases intra-vasculature positioning of the probe 70.

Figure 3:
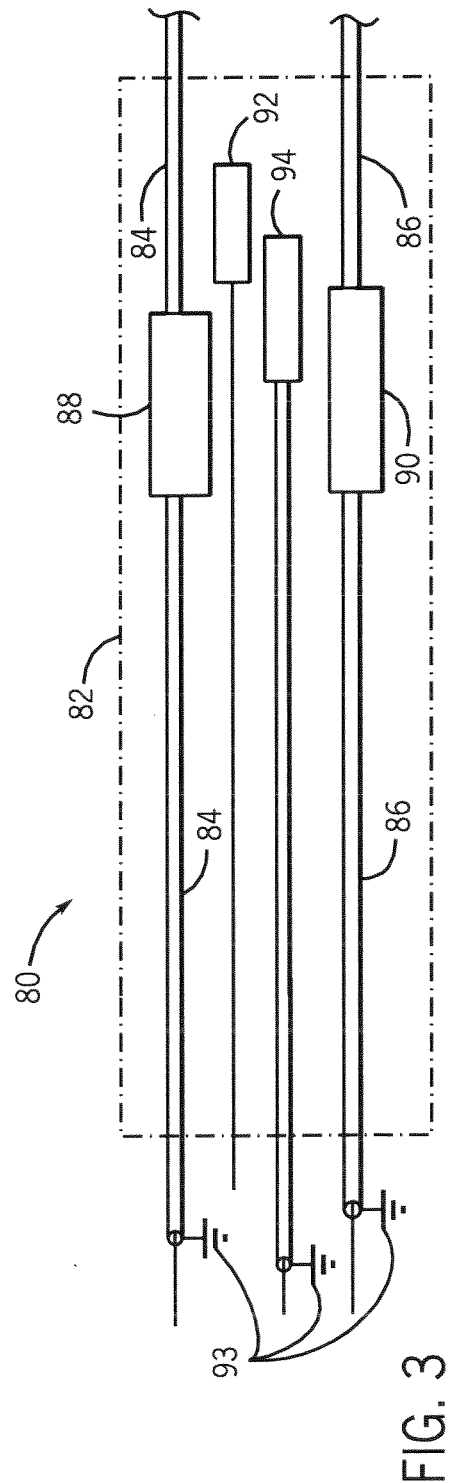
FIG. 3 is a cross-sectional view of FIG. 2 of a catheter shaft taken along line 3-3 of FIG. 2.

Referring to FIG. 3, a cross-sectional view of FIG. 2 taken along line 3-3 is shown. The catheter 82 carries two thin coaxial RF lines 84, 86 connected to the RF coils to transmit received MR data signals to the MRI system 10. The coaxial RF lines 84, 86 have a diameter preferably less than 0.5 mm. Two tuning micro-capacitors 88, 90 are connected to each RF line 84, 86 to prevent direct current from reaching the RF coils and to approximately tune the RF coils to the resonant frequency of the MRI system 10. As the final size of the probe 70 varies according to the surrounding anatomy, external circuits may be used to tune and match each of the RF coils to improve RF sensitivity.

Catheter 82 also carries a thin quarter-wavelength balun 92 to reduce RF noise at the carrier frequency as well as to reduce inter-line coupling through the coaxial line grounds 93. Balun 92 is open-circuited at its distal end and preferably has a diameter less than 0.25 mm. Catheter 82 further carries a coaxial line 95 that transmits tracking data received by the tracking coil 94 to the MRI system 10.

Referring now to FIG. 4, an elevational view of a bar assembly 72 taken along line 4-4 of FIG. 2 is shown. An expandable bar 74 provides a support upon which a thin RF coil element 76 is attached. The RF coil element 76 is preferably constructed of a copper wire and preferably attaches to an edge of the expandable bar 74 facing away from the opposing expandable bar 74. The expandable bar 74 is constructed of a memory-type material that allows the material to be deformed by a compression force and to automatically return to a non-deformed position when the compression force is removed. In a preferred embodiment, the expandable bar 74 is constructed of nitinol or similar material(s).

For increased RF sensitivity outside the probe, RF coil element 76 is positioned along expandable bar 74 such that a pre-determined distance or gap 96 is formed therebetween. The constant distance is maintained by using a known-thickness of an insulating material with a known dielectric constant. In a preferred embodiment, this is performed by using known-thickness heat-shrink tubing, which is wrapped about the expandable bar. In this manner, an RF field generated by the RF coil element 76 may be increased in a direction away from the surface of probe 70 and into the target tissue. Several layers of heat-shrink tubing 98 are disposed around the RF coil element 76 and the expandable bar 74 to attach the RF coil element 76 to the expandable bar 74 and to provide a hermetical seal from moisture. Heat-shrink tubing 98 also substantially electrically isolates the expandable bar 74 and the RF coil element 76 from blood or soft-tissue walls.

Referring to FIG. 5, a side elevational schematic view of the probe 70 in a compressed position in accordance with the present invention is shown. The bar assemblies 72 are compressible such that probe 70 may be positioned within a sheath 100 for insertion into an imaging subject. Sheath 100 is constructed to enclose the bar assemblies 72 and applies a compression force upon the bar assemblies 72 during insertion into the imaging subject and translation to a target tissue to be imaged. Preferably, sheath 100 is a 9 Fr. sheath with a length that exceeds a distance from an insertion point to the target tissue to be imaged. Probe 70 is compressed within sheath 100 as the collective assembly is translated through the vasculature to the target tissue or blood flow.

In contrast and referring to FIG. 6, a side elevational schematic view of the probe 70 in an expanded position in accordance with the present invention is shown. When the target tissue within the vascular system is reached, the sheath 100 is retracted to expose probe 70 and to allow the bar assemblies 72 to automatically expand. The bar assemblies 72 expand and, preferably, to substantially match an inner diameter of a vasculature or other target tissue in which the probe is placed. In an expanded position, the probe 70 permits fluid or blood flow between the bar assemblies 72 along flow vectors 102 to reduce occlusion that may occur in the vasculature. Allowing blood flow to pass through the probe 70 increases the amount of time in which the probe 70 may be expanded within the vasculature. During data acquisition, movements of probe 70 are actively tracked and monitored using signals received from the MR tracking coil 94. In this regard, probe 70 movements may be used to gate the data acquisition, and imaging artifacts caused by probe 70 movements within a pulsating vascular volume of interest may be taken into account and, preferably, reduced.

Advantages in using an RF probe constructed according to the present invention include a sheath-deployable expandable RF coil and the use of RF conductor spacing from a metal surface to force EM field projection outside the probe. Other advantages include multi-channel reception in an interventional coil and use of an integrated imaging and tracking coil to reduce motion artifacts or blurring in images taken within moving structures. In addition, the tracking coil is designed to provide feedback to assist with navigating to the target anatomy when the expandable RF coil is compressed in the sheath. That is, the tracking coil provides feedback independent of the expansion/compression of the RF coil. Furthermore, use of the RF probe constructed according to the present invention is particularly advantageous for acquiring MR images of the atrium or ventricles of the heart, and imaging the pulmonary vein anatomy.

An RF coil constructed according to the present invention is optimally used in a four-channel, or greater-number of channels, phased-array together with a two-channel surface coil. The RF coil provides a SNR that allows for faster data acquisitions or higher spatial resolution imaging, which is important in imaging the heart or heart anatomy where imaging times are limited by patient breath-holding tolerance and/or when resolution is limited by the irregularity of cardiac motion over time. Image acquisition may be gated by using data received from the MR tracking coil. In this manner, image artifacts may be reduced. Furthermore, commercial benefits may be realized with the increased utilization of MR imaging to guide or monitor therapeutic processes in the heart. For commercial applications, high spatial and temporal resolution are required as well as a high contrast-to-noise, for example, tissue temperature monitoring.

Therefore, in accordance with one embodiment of the present invention, a probe is disclosed that includes a self-expanding housing insertable into a subject to be imaged and constructed to permit fluid flow therethrough. A plurality RF coils are included that are attached to the housing.

In accordance with another embodiment of the present invention, an MRI apparatus is disclosed that includes a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images. The RF coil assembly includes a catheter configured for insertion into a blood flow and constructed to automatically expand to an expanded position from a compressed position. The RF coil assembly also includes a plurality of RF coils connected to the catheter and configured to acquire MR data. Further, the RF coil assembly also includes a tracking coil connected to the catheter and configured to indicate RF coil assembly location and movement within an imaging subject.

In accordance with yet another embodiment of the present invention, a method of using an MR imaging device is disclosed that includes inserting an intra-cardiac MR imaging device into a sheath configured for insertion into an imaging subject to be scanned, the imaging device comprising an MR tracking coil and a pair of RF coils attached to an auto-expandable former. The method includes positioning the imaging device within the imaging subject to be scanned and retracting the sheath to allow the former to automatically expand the pair of RF coils to an expanded position.

The present invention has been described in terms of the preferred embodiment, and it is recognized that equivalents, alternatives, and modifications, aside from those expressly stated, are possible and within the scope of the appending claims.

What is claimed is:
1. An MRI apparatus comprising:
   a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images, the RF coil assembly comprising:
- an intra-cardiac catheter configured for insertion into a blood flow and constructed to automatically expand to an expanded position from a compressed position;
- a plurality of RF coils connected to the catheter and configured to acquire MR data; wherein a constant thickness gap filled with an insulating material formed between the plurality of RF coils and an expandable portion of the catheter is configured to increase RF sensitivity away from the catheter; wherein the intra-cardiac catheter is configured to automatically expand the plurality of RF coils to an expanded position from a compressed position;
- a tracking coil connected to the catheter and configured to indicate RF coil assembly location and movement within an imaging subject;
- wherein the tracking coil is configured to transmit signals indicating the location and movement of the RF coil assembly to the MRI system to facilitate MR data acquisition gating; and
- wherein the MRI system is configured to gate MR data acquisition during imaging based on the location and movement of the RF coil assembly.

2. The MRI apparatus of claim 1 wherein the catheter expands to substantially match an inner diameter of a target tissue in which the probe is placed.

3. The MRI apparatus of claim 1 wherein the catheter is configured to allow fluid flow vectors pass through the catheter.

4. The MRI apparatus of claim 1 wherein the plurality of RF coils includes a first RF coil and a second RF coil.

5. The MRI apparatus of claim 4 wherein the catheter includes a first set of bars attached to the first RF coil and a second set of bars attached to the second RF coil.

6. The MRI apparatus of claim 1 further comprising a sheath configured to receive the RF coil assembly therein for insertion into an imaging subject.

7. The MRI apparatus of claim 6 wherein the catheter is configured to auto-expand upon sheath retraction from the RF coil assembly.

8. The MRI apparatus of claim 7 wherein the catheter is constructed of a memory-type material.

9. A method of using an MR imaging device, the method comprising:
- inserting an intra-cardiac MR imaging device into a sheath configured for insertion into an imaging subject to be scanned, the imaging device comprising an MR tracking coil and comprising a pair of RF coils attached to an auto-expandable former; wherein a constant thickness gap filled with an insulating material formed between the pair of RF coils and the auto-expandable former is configured to increase RF sensitivity away from the auto-expandable former;
- positioning the imaging device within the imaging subject to be scanned;
- retracting the sheath to allow the former to automatically expand the pair of RF coils to an expanded position;
- acquiring tracking data from the MR tracking coil representing position and movement of the imaging device during imaging; and
- gating data acquisition during imaging based on the tracking data to reduce imaging artifacts.

10. The method of claim 9 wherein the former is constructed to allow fluid subflow passage therethrough.

11. The method of claim 9 further comprising actively tracking movement of the imaging device during image scanning to monitor movement of the imaging device.

12. The method of claim 9 further comprising the step of receiving tracking feedback from the tracking coil while navigating to a target anatomy prior to retracting the sheath therefrom.

\* \* \* \* \*